US00PP17069P3

(12) United States Plant Patent
Redman

(10) Patent No.: US PP17,069 P3
(45) Date of Patent: Aug. 29, 2006

(54) ***CHRYSANTHEMUM* PLANT NAMED 'EXTRAVAGANZA TIME'**

(50) Latin Name: *Chrysanthemum morifolium*
Varietal Denomination: Extravaganza Time

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 11/146,388

(22) Filed: Jun. 6, 2005

(65) Prior Publication Data

US 2005/0273895 P1 Dec. 8, 2005

Related U.S. Application Data

(60) Provisional application No. 60/578,009, filed on Jun. 7, 2004.

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

2003/0056259 P1 3/2003 Boeder ..... Plt./286

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Extravaganza Time', having a good uniform canopy of white and purple single flowers with a light green disc. The new variety has a uniform spreading habit with a good foliage presentation.

1 Drawing Sheet

Latin name of the genus and species: Botanical classification: *Chrysanthemum morifolium.*

Variety denomination: The new *Chrysanthemum* variety denomination is 'Extravaganza Time'.

BACKGROUND OF THE INVENTION

The present invention comprises a new and distinct cultivar of *chrysanthemum* botanically known as *Chrysanthemum morifolium,* and referred to by the variety name 'Extravaganza Time'.

'Extravaganza Time', identified as '21941-0', originated from a cross in a controlled breeding program in Chichester, West Sussex, United Kingdom. The female parent of the variety is '20934-0', an undistributed and unpatented seedling and the male parent of the variety is '20713-0', an undistributed and unpatented seedling.

The new variety 'Extravaganza Time' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Extravaganza Time' is a pot type of *Chrysanthemum* plant variety having large white and purple bi-color flowers with a green disc.

COMPARISON WITH FEMALE PARENT

Plants of the new *Chrysanthemum* variety 'Extravaganza Time' are similar to the parent '20934-0' in plant habit and growth rate. However in side-by-side comparisons in Chichester, West Sussex, United Kingdom, under commercial practice, plants of the new *chrysanthemum* variety 'Extravaganza Time' differed from plants of the parent '20934-0' in the following characteristics:

1. The new variety 'Extravaganza Time' produces large white and purple bi-color flowers whereas the parent '20934-0' produces white flowers.
2. Plants of the new variety 'Extravaganza Time' have larger and taller inflorescence than plants of '20934-0'.
3. Plants of the new variety 'Extravaganza Time' have a quicker response time to the plants of '20934-0'.

COMPARISON WITH MALE PARENT

Plants of the new *Chrysanthemum* variety 'Extravaganza Time' are similar to the parent '20713-0' in plant habit and growth rate. In side-by-side comparisons in Chichester, West Sussex, United Kingdom, under commercial practice, plants of the new *chrysanthemum* variety 'Extravaganza Time' differed from plants of the parent '20713-0' in the following characteristics:

1. The new variety 'Extravaganza Time' produces large white and purple bi-color flowers whereas the parent '20934-0' produces white flowers.
2. Plants of the new variety 'Extravaganza Time' have larger and taller inflorescence than plants of '20934-0'.
3. Plants of the new variety 'Extravaganza Time' have a quicker response time to the plants of '20934-0'.

COMPARISON WITH OTHER VARIETIES

Plants of the new *Chrysanthemum* variety 'Extravaganza Time' are similar to the variety 'Lunar Time' (U.S. Plant patent application Publication No. 2003/0056259) in plant habit and growth rate. However, in side-by-side comparisons in Chichester, West Sussex, United Kingdom, under commercial practice, plants of the new *chrysanthemum* variety 'Extravaganza Time' differed from plants of 'Lunar Time' in the following characteristics:

1. The new variety 'Extravaganza Time' produces white and purple single flowers whereas 'Lunar Time' produces cream and purple flowers.
2. Plants of the new variety 'Extravaganza Time' have smaller and shorter inflorescence than plants of 'Lunar Time'.
3. The new variety 'Extravaganza Time' does not produce pollen whereas 'Lunar Time' has pollen on the disc florets.

BRIEF DESCRIPTION OF ILLUSTRATIONS

Typical specimens of the plant and flowers for the new *Chrysanthemum* variety 'Extravaganza Time' are shown in the accompanying digital photograph. The colors shown are as true as possible within the usual limits of this kind of illustration.

FIG. 1 is a whole plant view of the new variety 'Extravaganza Time' grown in a pot. The plant shown in the illustration is 56 days from the commencement of Short Days.

DETAILED BOTANICAL DESCRIPTION

The following description of the new *Chrysanthemum* variety 'Extravaganza Time' is of plants grown in a greenhouse in Chichester, West Sussex, United Kingdom, in the month of September. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gram per liter. To produce a commercial product the plants may be pinched once with the center bud removed. The typical container size for commercial growth is 1 liter. It has been observed that the shelf life of the new variety is about 21 days with a response time of about 7.5 weeks. The new variety is suitable for growth in a temperature range of 15° C. to 25° C.

The new variety may be produced as a spray. The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 22.
Width (cm): 32.
Stem:
- *Length* (*cm*).—6.0.
- *Diameter* (*cm*).—0.5.
- *Texture.*—Slightly pubescent.
- *Color.*—138B.

Branching characteristics: Upright and free branching.
Lateral branches:
- *Length* (*cm*).—12.
- *Diameter* (*cm*).—0.3.
- *Texture.*—Slightly pubescent.

Number of breaks from pinch: 4.
Response time: 52 days.
Vigor: Medium to tall.
Shelf life: 21 days.
Life of blooms: 21 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings. The plants were grown for 2 weeks in Long Day conditions (20 hours of light) and then transferred to Short Day conditions (13 hours of dark).
Propagation:
- *Type.*—Vegetative Propagation Via Stem Cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 12.
Compound or single: Single.
Arrangement of leaves: Alternate.
- *Shape of leaf.*—Typically 5 lobed.
- *Size of leaf.*—Width (cm): 4. Length (cm): 6.5.
- *Leaf apex.*—Acute.
- *Base.*—Obtuse.
- *Attachment.*—Petioled.
- *Aspect.*—Slightly undulating.
- *Margin.*—Lobed.
- *Surface characteristics.*—Top: Slightly pubescent. Bottom: Pubescent.

Petiole:
- *Color.*—137C.
- *Length* (*cm*).—1.3.
- *Diameter* (*cm*).—0.3.

Venation:
- *Color.*—Upper side: 138B. Under side: 138C.

Color:
- *Mature leaf, upper side.*—137C; under side: 138B.
- *Young leaf, upper side.*—137B; under side: 138B.

Flower

Flower appearance: Matte.
Flower type: Single.
Flower form: Slightly cupped.
Flower shape: Circular.
Flowering habit: Cyme.
Number of blossoms per branch: 5.
Typical and observed flowering season: January to December.
Inflorescence form: Cyme.
- *Depth of fully expanded blossoms* (*cm*).—1.5.
- *Diameter of fully expanded blossoms* (*cm*).—8.

Phyllaries:
- *Number.*—20.
- *Color.*—138B.
- *Length* (*cm*).—0.6.
- *Width* (*cm*).—0.1.
- *Texture/appearance.*—Pubescent.

Peduncle:
- *Length* (*cm*).—12.
- *Diameter* (*cm*).—0.3.

*Angle from stem* (*degrees*).—20.
*Color.*—138A.
*Surface.*—Slightly pubescent.
*Habit.*—Slightly undulating.
*Strength.*—Moderately strong.

Pedicel:
*Length.*—Terminal (cm): 2; lateral (cm): 4.
*Diameter* (*cm*).—0.2.
*Color.*—138B.
*Surface.*—Slightly pubescent.
*Habit.*—Slightly undulating.
*Strength.*—Moderately strong.

Ray florets:
*Form/shape.*—Straight with rounded tip and tapered at the base.
*Texture/appearance.*—Matte.
*Number per flower.*—22.
*Length* (*cm*).—4. Width (cm): 0.7.
*Apex.*—Rounded.
*Base.*—Tapered.
*Margin.*—Entire.

Disc florets:
*Form/shape.*—Cylindric.
*Texture/appearance.*—Shiny.
*Number per flower.*—>200.
*Length* (*cm*).—0.5; Width (cm): 0.1.
*Diameter of disc* (*cm*).—1.3.

Fragrance: None.

Flower bud (at onset of color):
*Length* (*cm*): 1.
*Diameter* (*cm*).—1.
*Form/shape.*—Globular.

General flower color:
1. *Ray florets, upper side.*—Immature: 64B from center towards the base and 158A towards the apex. Mature: 63B from center towards the base and 155A towards the apex. Older/Fading: 64D from center towards the base and 155A towards the apex.
2. *Ray florets, under side.*—Immature: 63A from center towards the base and 158A towards the apex. Mature: 63B from center towards the base and 155A towards the apex. Older/Fading: 63C from center towards the base and 155A towards the apex.
3. *Disc florets.*—Immature: 144C. Mature: 151A. Older/Fading: 151C.
4. *Bud.*—158A towards the apex and 64A from center towards the base.

Flower progression with age: The flower form does not change but there is a slight color fading with age.

Reproductive Organs

Gynoecium present on ray and disc florets.

Ray florets per individual flower: Pistillate.
*Pistil number.*—22.
*Stigma color.*—151D.
*Stigma shape.*—Forked.
*Style color.*—151C.
*Style length* (*cm*).—0.3.

Disc florets per individual flower: Pistillate.
*Pistil number.*—>200.
*Stigma color.*—151D.
*Stigma shape.*—Forked.
*Style color.*—151C.
*Style length* (*cm*).—0.3.

Androecium not observed.

Fruit and seeds: None observed to date.

What is claimed is:

1. A new and distinct variety of *Chrysanthemum* plant, substantially as described and illustrated herein.

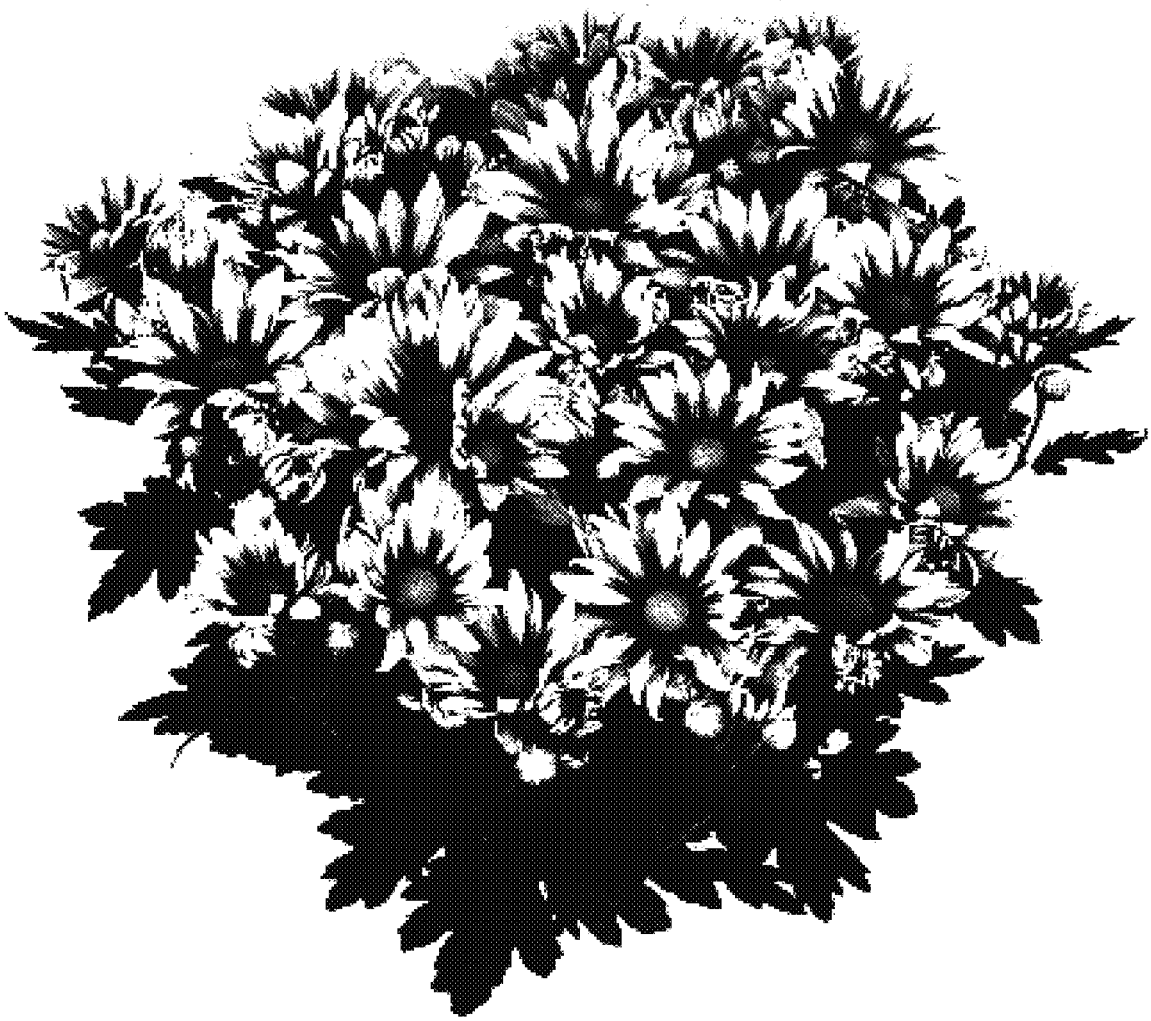

* * * * *